United States Patent
Musial et al.

(10) Patent No.: US 7,953,561 B2
(45) Date of Patent: May 31, 2011

(54) RESONANCE TEST SYSTEM

(75) Inventors: Walter Musial, Boulder, CO (US); Darris White, Superior, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 524 days.

(21) Appl. No.: 10/520,011

(22) PCT Filed: Jul. 3, 2002

(86) PCT No.: PCT/US02/20991
§ 371 (c)(1), (2), (4) Date: Dec. 29, 2004

(87) PCT Pub. No.: WO2004/005879
PCT Pub. Date: Jan. 15, 2004

(65) Prior Publication Data
US 2006/0037402 A1  Feb. 23, 2006

(51) Int. Cl.
*G01L 5/00* (2006.01)
*G06F 11/00* (2006.01)
(52) U.S. Cl. ............. 702/42; 702/56; 702/141; 702/188
(58) Field of Classification Search ............. 702/42, 702/56, 141, 179–190, 43, 44, 58–62, 116–122; 73/808, 789, 798, 579, 849, 788, 794, 795, 73/806
See application file for complete search history.

(56) References Cited

U.S. PATENT DOCUMENTS

| | | | |
|---|---|---|---|
| 3,664,179 A | 5/1972 | Danko et al. | |
| 3,772,913 A | 11/1973 | Zell et al. | |
| 4,519,053 A | 5/1985 | Bedenbender et al. | |
| 4,924,706 A | 5/1990 | Moore | |
| 4,955,269 A | 9/1990 | Kendig et al. | |
| 5,136,200 A | 8/1992 | Takizawa et al. | |
| 5,290,148 A | 3/1994 | Tsunoda et al. | |
| 5,425,276 A | 6/1995 | Gram et al. | |
| 5,445,027 A | 8/1995 | Zorner | |

(Continued)

FOREIGN PATENT DOCUMENTS

DE  10112316 A1  12/2001

(Continued)

OTHER PUBLICATIONS

Musial et al, Resonance Test System for Wind Turbine Blades Using Hydraulic Excitation, powerpoint, Sep. 20, 2001.

(Continued)

*Primary Examiner* — Andrew Schechter
*Assistant Examiner* — Phuong Huynh
(74) *Attorney, Agent, or Firm* — W. LaNelle Owens; John C. Stolpa; Paul J. White

(57) ABSTRACT

An apparatus (10) for applying at least one load to a specimen (12) according to one embodiment of the invention may comprise a mass (18). An actuator (20) mounted to the specimen (12) and operatively associated with the mass (18) moves the mass (18) along a linear displacement path (22) that is perpendicular to a longitudinal axis of the specimen (12). A control system (26) operatively associated with the actuator (20) operates the actuator (20) to reciprocate the mass (18) along the linear displacement path (22) at a reciprocating frequency, the reciprocating frequency being about equal to a resonance frequency of the specimen (12) in a test configuration.

20 Claims, 5 Drawing Sheets

U.S. PATENT DOCUMENTS

| | | | |
|---|---|---|---|
| 5,517,128 A | 5/1996 | Heninger | |
| 5,789,666 A * | 8/1998 | Bayer et al. | 73/105 |
| 6,082,198 A | 7/2000 | Sabourin et al. | |
| 6,098,465 A * | 8/2000 | Matsumoto et al. | 73/808 |
| 6,102,664 A | 8/2000 | Nguyen | |
| 6,205,863 B1 * | 3/2001 | Ishii et al. | 73/805 |
| 6,240,792 B1 | 6/2001 | Elsesser | |
| 6,378,951 B1 | 4/2002 | Bouyoucos et al. | |
| 6,441,571 B1 | 8/2002 | Ibuki et al. | |
| 6,442,534 B1 * | 8/2002 | Au et al. | 706/1 |
| 6,601,456 B1 * | 8/2003 | Davidson et al. | 73/808 |
| 6,718,833 B2 * | 4/2004 | Xie et al. | 73/812 |
| 6,732,591 B2 * | 5/2004 | Miles et al. | 73/808 |
| 7,233,476 B2 * | 6/2007 | Goldenberg et al. | 361/140 |
| 2002/0017144 A1 | 2/2002 | Miles | |
| 2002/0038987 A1 * | 4/2002 | Magnussen et al. | 310/323.16 |
| 2005/0011263 A1 * | 1/2005 | Harris | 73/579 |

FOREIGN PATENT DOCUMENTS

| | | |
|---|---|---|
| EP | 0518262 A2 | 12/1992 |
| GB | 2060179 A | 4/1981 |
| GB | 2071782 | 9/1981 |

OTHER PUBLICATIONS

Supplemental EP Search Report, EP 027497542, dated Feb. 12, 2008, PCT/US02/20991, International Filing Date Jul. 2, 2002.

Written Opinion dated Feb. 7, 2005, PCT/US02/20991, International Filing Date Jul. 2, 2002.

* cited by examiner

US 7,953,561 B2

RESONANCE TEST SYSTEM

CONTRACTUAL ORIGIN OF THE INVENTION

The United States Government has rights in this invention pursuant to Contract No. DE-AC36-99GO10337 between the U.S. Department of Energy and the Midwest Research Institute.

TECHNICAL FIELD

This invention relates to systems for applying structural loads to specimens and more specifically to a system for applying structural loads to wind turbine blades.

BACKGROUND ART

Wind-powered generator systems are well-known in the art and have been used for decades for generating electrical power from wind energy. While numerous configurations exist and have been used with varying degrees of success, most wind-powered generator systems utilize a rotor or impeller that is configured to rotate in a prevailing wind. An electrical generator connected to the rotor is rotated by the rotor and produces useful electrical power from the rotational movement of the rotor.

A commonly used rotor design or configuration resembles an aircraft propeller in that it comprises a plurality of long, slender turbine blades (typically three, although a greater or lesser number of blades may also be used) mounted to a hub. The hub is in turn mounted to a support structure or mainframe so that the hub and blades are free to rotate with respect to the mainframe. The hub is typically mounted to shaft which drives one or more electrical generators. In order to extract a meaningful amount of energy from the wind, it is usually necessary to provide the rotor with long blades. Consequently, the rotor and mainframe must be mounted on a high tower or pylon in order to provide sufficient clearance for the rotating rotor blades as well as to elevate the rotor blades above the turbulent air caused by terrain variations, buildings, and other obstructions on the ground. The mainframe is also usually pivotally mounted to the tower or pylon to allow the rotor to be directed into the prevailing wind.

There is a trend for wind generator systems to become increasingly larger. Unfortunately, however, the larger blades associated with larger wind generator systems are subjected to greater static and dynamic loads. As a result, it is very desirable, and often necessary, to test in advance a proposed blade design to ensure that it will be capable of withstanding the expected loads without structural failure. It is also important to evaluate the fatigue resistance of the blade design.

Generally speaking, wind turbine blades are tested by applying loads to the blade in various directions. For example, one type of load is applied in a direction perpendicular to the longitudinal or long axis of the blade, and is often referred to as a bending load, or as a flap load in the wind turbine field. Another type of load is also applied in a direction perpendicular to the longitudinal axis, but also perpendicular to the direction of the applied bending or flap load, in order to assess the structural properties of the blade in the transverse or rotational direction. Such loads are often referred to as transverse loads, or as lead-lag loads in the wind turbine field. The load applied to the blade in a given direction may be time-invariant or "static." Alternatively, the load may be made to vary with time, in which case the load is often referred to as "cyclic." Static loads are generally useful in evaluating the stiffness and ultimate strength of the blade, whereas cyclic loads are generally useful in evaluating the fatigue resistance of the blade.

Several different types of test apparatuses have been developed and are being used to apply loads to wind turbine blades. One type of test apparatus uses hydraulic actuators to apply the desired loads to the blade. This type of apparatus is advantageous in that it can be used to apply loads in any desired direction by simply mounting the hydraulic actuators at the desired positions on the blade and by orienting the actuators in the appropriate directions. Loads in more than one direction may be applied simultaneously with such apparatus, which often reduces the time required for testing. In addition, both static and cyclical loads may be applied by such apparatus.

Unfortunately, however, hydraulic testing systems of the type just described are not readily scalable, and it is difficult to use such an apparatus to test larger blades. For example, larger blades require larger deflections, thereby increasing the amount of hydraulic fluid that must be pumped to the actuators. While larger pumps can be used, there is a limit to the maximum pump size that can be practically used, both from a power requirement standpoint and from the standpoint of pump system cost. It is also difficult to provide actuators capable of producing the larger blade deflections. Even if such large-deflection actuators can be provided, larger blade deflections usually require more time to achieve a given number of load cycles.

Another system for placing loads on wind turbine blades uses a rotating eccentric mass to vibrate the blade along the longitudinal axis. Thus, a rotating mass system may be used to apply a cyclical bending or flap load to the blade. The system is designed so that the rotational speed of the mass vibrates the blade at about the resonance frequency of the blade in the longitudinal direction. Accordingly, such systems are often referred to as resonant test systems. The resonant vibration of the blade reduces the amount of energy required to apply the cyclical loads, thus is theoretically advantageous for testing larger blades. Unfortunately, however, the rotating mass also places axial loads on the blade which, at the forces required to maintain significant fatigue stresses in the longer blades, can become unacceptably large. Another problem with a rotating mass system is that it has proven difficult to simultaneously apply both bending and transverse loads to the blade. That is, while such a rotating mass system may be used to apply cyclic transverse or "lead-lag" loads to the blade by re-orienting the position of the rotating mass with respect to the blade, it is not generally practical to operate both types of rotating mass systems simultaneously. Instead, the usual practice is to perform the two tests (e.g., bending and transverse vibrational tests) at different times.

DISCLOSURE OF INVENTION

Apparatus for applying at least one load to a specimen according to one embodiment of the invention may comprise a mass. An actuator mounted to the specimen and operatively associated with the mass moves the mass along a linear displacement path that is perpendicular to a longitudinal axis of the specimen. A control system operatively associated with the actuator operates the actuator to reciprocate the mass along the linear displacement path at a reciprocating frequency, the reciprocating frequency being about equal to a resonance frequency of the specimen in a test configuration.

Also disclosed is a method for vibrating a specimen that comprises: Mounting a mass to the specimen so that the mass can be reciprocated along a linear displacement path that is perpendicular to the longitudinal axis of the specimen; and reciprocating the mass along the linear displacement path at a reciprocation frequency that is about equal to a resonance frequency of the specimen in a test configuration.

BRIEF DESCRIPTION OF THE DRAWINGS

Illustrative and presently preferred embodiments of the invention are shown in the accompanying drawings in which.

BEST MODES FOR CARRYING OUT THE INVENTION

Figure 1:
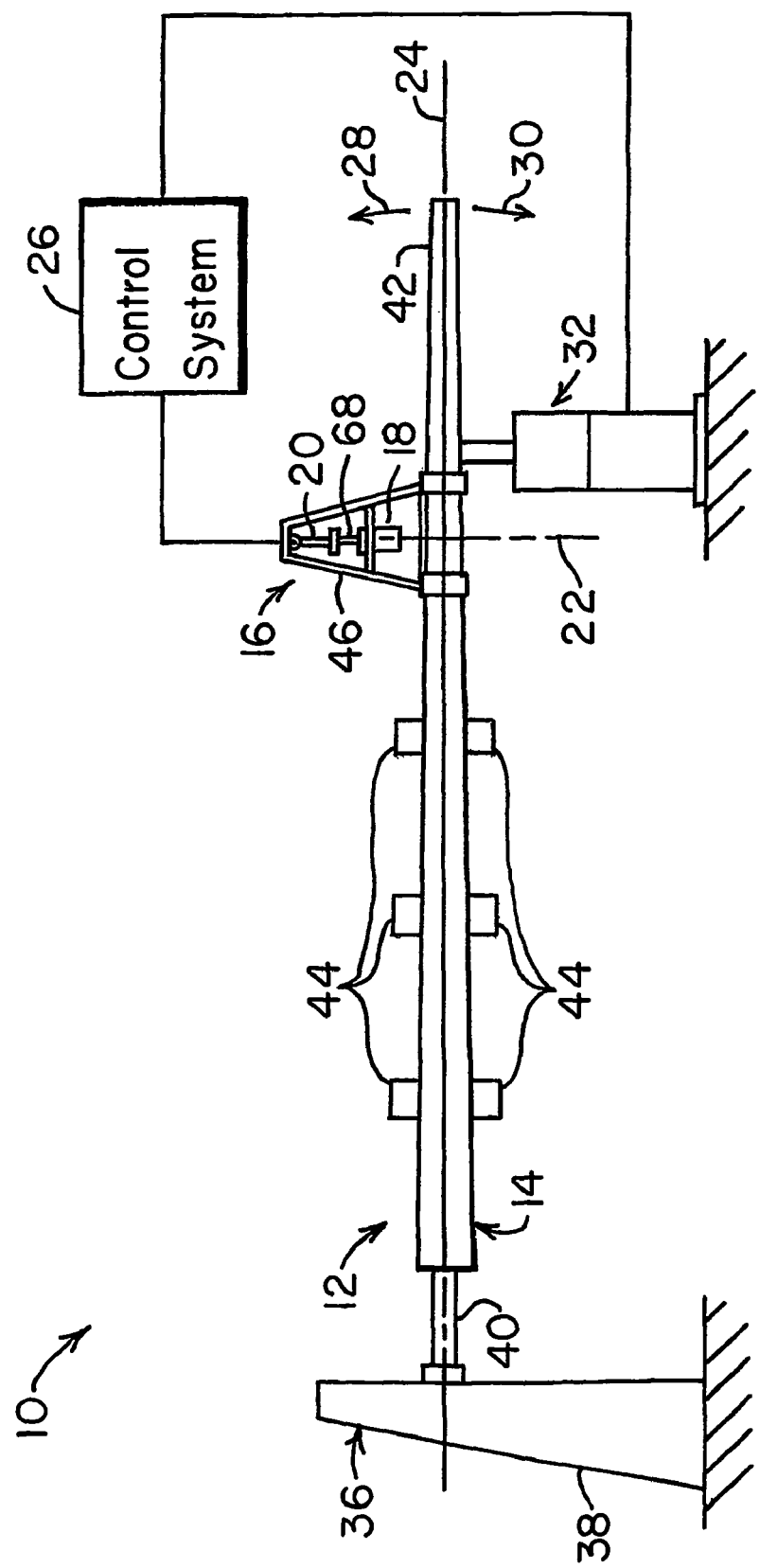
FIG. 1 is a side view in elevation of an apparatus for applying a load to a specimen according to one embodiment of the invention.

Apparatus 10 for applying at least one load to a specimen 12, such as a wind turbine blade 14, is best seen in FIGS. 1-4 and may comprise a resonant actuator system 16 having a mass 18 that is operatively associated with an actuator 20. The actuator 20 moves the mass 18 along a linear displacement axis or path 22 that is perpendicular to a longitudinal axis 24 of the wind turbine blade 14. A control system 26 operatively associated with the actuator 20 operates the actuator 20 to reciprocate the mass 18 along the linear displacement path 22 at a reciprocating frequency that is about equal to a resonance frequency of the specimen 12 (e.g., wind turbine blade 14) in a test configuration. The reciprocating mass 18 causes the wind turbine blade 14 to vibrate along the longitudinal axis 24, i.e., in the directions indicated by arrows 28 and 30, which results in the application to the specimen 12 (e.g., wind turbine blade 14) of bending or flap loads.

Figure 2:
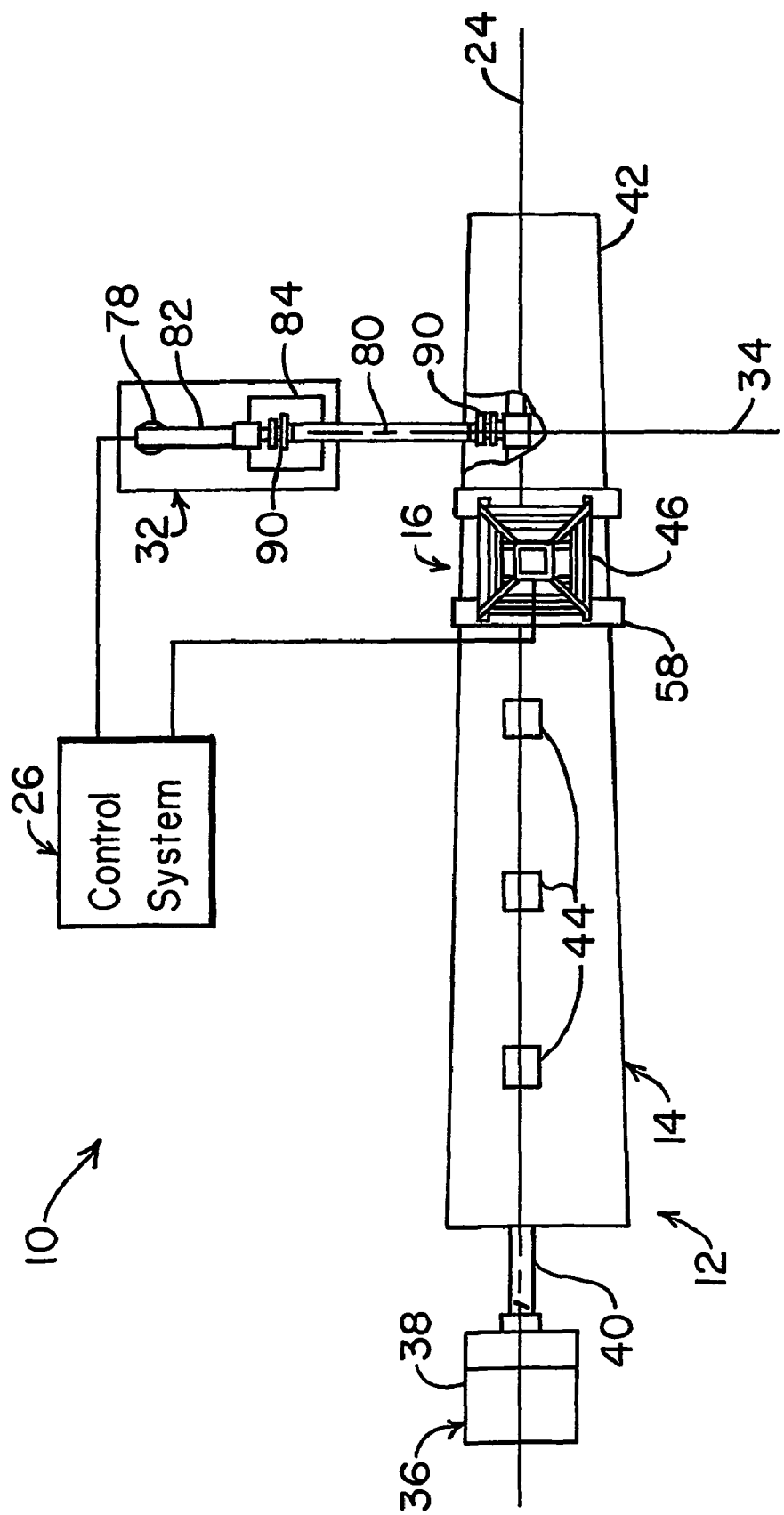
FIG. 2 is a plan view of the apparatus illustrated in FIG. 1.
Figure 3:
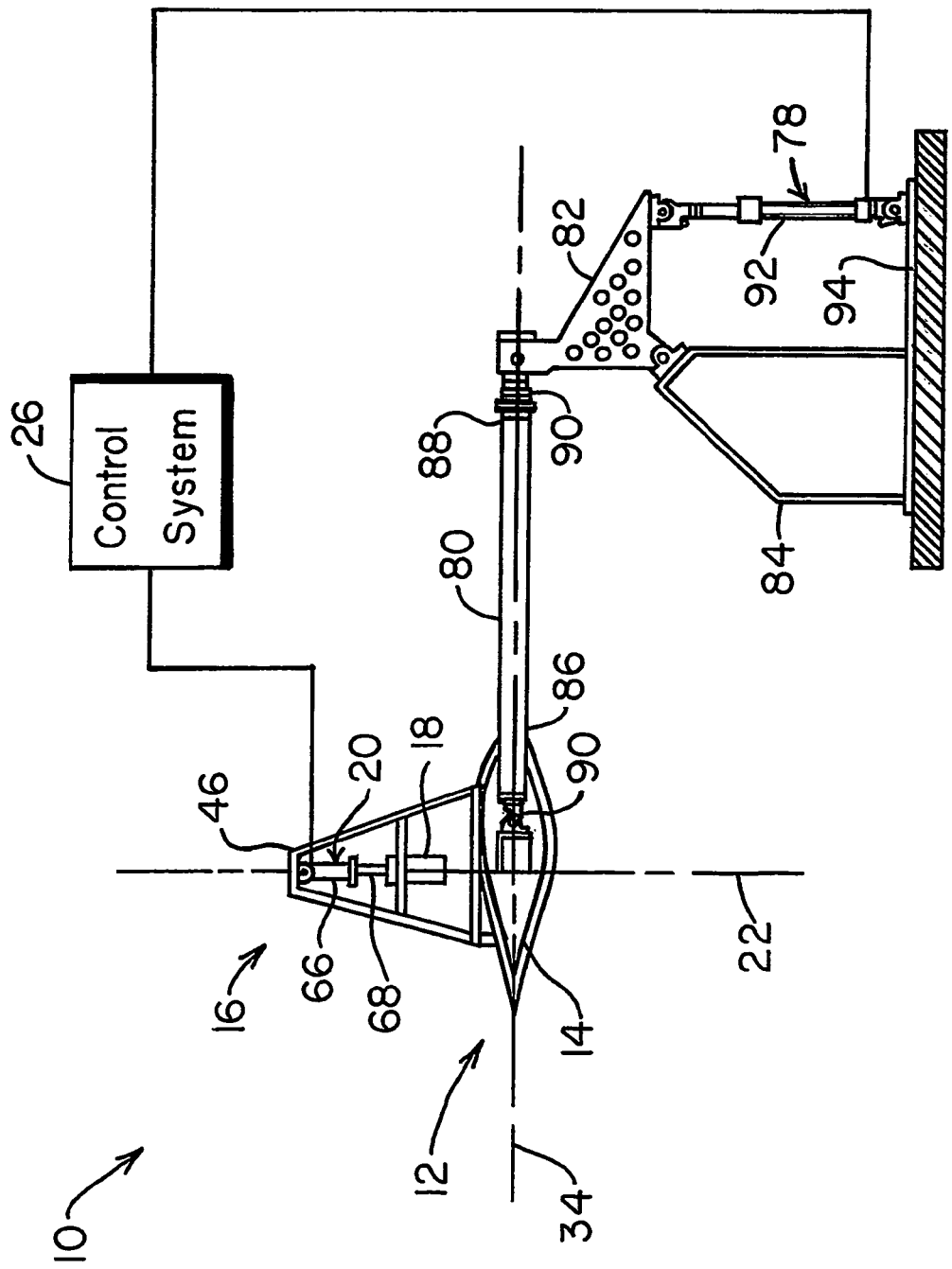
FIG. 3 is an end view of the apparatus illustrated in FIG. 1 more clearly showing the transverse actuator system.

It is generally preferred, but not required, that the apparatus 10 also be provided with a transverse load actuator system 32 for applying to the specimen 12 a load in a transverse direction 34 (FIGS. 2 and 3). Such loads are referred to herein as transverse loads or "lead-lag" loads. Like the resonant actuator system 16, the transverse load actuator system 32 is operatively associated with the control system 26 which controls the operation thereof. For example, in one embodiment, the control system 26 operates the transverse load actuator system 32 simultaneously with the resonant actuator system 16. In this operational situation, the load applied by the transverse load actuator system 32 is applied at substantially the reciprocating frequency of the resonant actuator system 16. Alternatively, and as will be described in greater detail below, the control system 26 may operate the transverse load actuator 20 separately from the resonant actuator system 16.

The apparatus 10 may be operated as follows to place one or more structural loads on the specimen 12 under test. Assuming that a suitable specimen 12, such as a rotor or turbine blade 14, has been provided, the specimen 12 (e.g., blade 14) is mounted in a suitable test fixture 36. By way of example, in one embodiment, the test fixture 36 may comprise a rigid support or mount 38 for fixedly supporting the root end 40 of the blade 14. The resonant actuator system 16 is mounted to the blade 14 at a position intermediate the root 40 and tip 42 of the blade 14 in the manner best seen in FIGS. 1 and 2. As will be described in greater detail below, it is generally preferred, but not required, to mount one or more static masses 44 to the blade 14. In one embodiment, the static masses 44 modify the loads applied to the blade 14 so that the blade loading will better approximate the expected in-service loads. At this point, the control system 26 may be activated to operate the resonant actuator system 16. More specifically, the control system 26 operates the actuator 20 to reciprocate the mass 18 at a reciprocation frequency that is about equal to the resonant frequency of the specimen 12 (e.g., blade 14) in the test configuration. The inertial loads placed on the actuator 20 by the reciprocating mass 18 are transferred to the blade 14, which results in the vibration of the blade 20 along the longitudinal axis 24. That is, the blade 14 will begin to be displaced in the directions indicated by arrows 28 and 30. Since the reciprocation frequency of the mass 18 is selected to be about equal to the resonant frequency of the blade 14 in the test configuration, the resonant actuator system 16 will easily produce substantial deflections (and resulting loads) of the blade 14 in the bending or flap direction. If a transverse load actuator system 32 is provided, the control system 26 may also actuate the transverse load actuator system 32 in order to simultaneously apply transverse loads to the vibrating blade 14.

One advantage of the present apparatus 10 is that it may be used to apply to the specimen 12 (e.g., blade 14) substantial deflections in the bending or flap directions with relatively low energy input. Accordingly, the present invention may be used to test sizable specimens 12 (e.g., wind turbine blades 14), but without experiencing some of the drawbacks associated with non-resonant hydraulic test systems, such as excessive pumping, actuator displacement, and energy requirements. Another advantage of the present invention is that it does not induce unwanted axial loads in the specimen 12, such as those associated with rotating mass resonant test systems.

Yet another advantage of the present invention is that a transverse load actuator system (e.g., 32) may be utilized to simultaneously apply transverse loads to the specimen 12. Thus, in a wind turbine blade testing application, the present invention may be used to provide highly representative loading to the wind turbine blade 14 in that the transverse or edge loads may be applied simultaneously with the bending or flap loads and in the proper phase relationship to one another. Other advantages of the present invention are associated with its relative mechanical simplicity of the various systems and devices and the fact that relatively small actuators may be used to impart sizable deflections and loads to the specimen 12.

Having briefly described the apparatus 10 for applying structural loads to a specimen 12, as well as some of its more significant features and advantages, the various embodiments of the apparatus 10 will now be described in detail. However, before proceeding with the description, it should be noted that while the apparatus 10 is shown and described herein as it may be used to apply structural loads to a wind turbine blade 14 (an example of a specimen 12), the present invention is not limited to use with any particular type of specimen 12. In fact, the present invention may be used to test any of a wide range of specimens 12 that are now known in the art or that may be developed in the future wherein it might be required or desired to place certain structural loads on the specimen 12 in accordance with the teachings of the present invention. Consequently, the present invention should not be regarded as limited to the particular specimen 12 (i.e., blade 14) and testing requirements and procedures shown and described herein.

With the foregoing considerations in mind, one preferred embodiment of apparatus 10 for placing structural loads on a specimen 12 is shown and described herein as it may be used to apply both bending (or flap) and transverse (or lead-lag) loads to a blade 14. The blade 14 extends along a longitudinal axis 24 and has a root end 40 and a tip end 42. The blade 14 may be of any conventional or yet-to-be developed design suitable for the intended application. The blade 14 may also be fabricated in accordance with conventional or yet-to-be developed techniques, as the case may be. However, since the particular design and/or structural configuration of the blade 14 are not necessary to understand or practice the present invention, the particular blade 14 that may be tested in conjunction with one preferred embodiment of the invention will not be described in further detail herein.

The test specimen 12 (e.g., blade 14) is affixed to a suitable support or test fixture 36 to allow the apparatus 10 of one embodiment of the present invention to apply the desired structural loads to the specimen 12. Any of a wide range of support or test fixtures 36 may be used to support the specimen 12 in a manner consistent with the desired purposes of the test, as would be obvious to persons having ordinary skill in the art after having become familiar with the teachings of the present invention. Consequently, the present invention should not be regarded as limited to any particular support or test fixture 36 for supporting the specimen 12 in any particular manner. However, by way of example, in one preferred embodiment, the support or test fixture 36 comprises a support mount 38 configured to fixedly receive the root end 40 of the blade 14 so that the root end 40 of blade 14 is rigidly supported thereby.

As mentioned above, the resonant actuator 16 is used to vibrate the specimen 12 along the longitudinal axis 24, thereby allowing the resonant actuator 16 to deflect the specimen 12 in the directions indicated by arrows 28 and 30. These deflections produce bending or flap loads in the specimen 12. The resonant actuator 16 may be mounted at any convenient position along the longitudinal axis 24 of the specimen 12, e.g., at any convenient position between the root end 40 and the tip end 42 of the blade 14. Accordingly, the present invention should not be regarded as limited to any particular mounting location for the resonant actuator 16. However, by way of example, in one embodiment, the resonant actuator 16 may be mounted between about $2/3$ to $3/4$ of the span of the blade 14. In this regard it should be noted that the $2/3$ to $3/4$ span positioning refers to the span of the design length of the blade 14, as opposed to any shortened span that may be utilized for testing. That is, in certain situations, the physical size of the testing facility may require that some portion (e.g., a few meters) of the tip of the blade 14 be removed so that the blade 14 can be fully contained within the test facility. If this is the case, the resonant actuator 16 may appear to be mounted closer to the tip of the blade 14 than is actually the case with respect to the design length of the blade (in that a portion of the tip end 42 was previously removed). Put another way, such shortened blade assemblies may be tested by the method and apparatus of the present invention even though the resonant actuator 16 is positioned closer to the tip of the foreshortened blade 14 than the $2/3$ to $3/4$ positioning referred to above.

Figure 4:
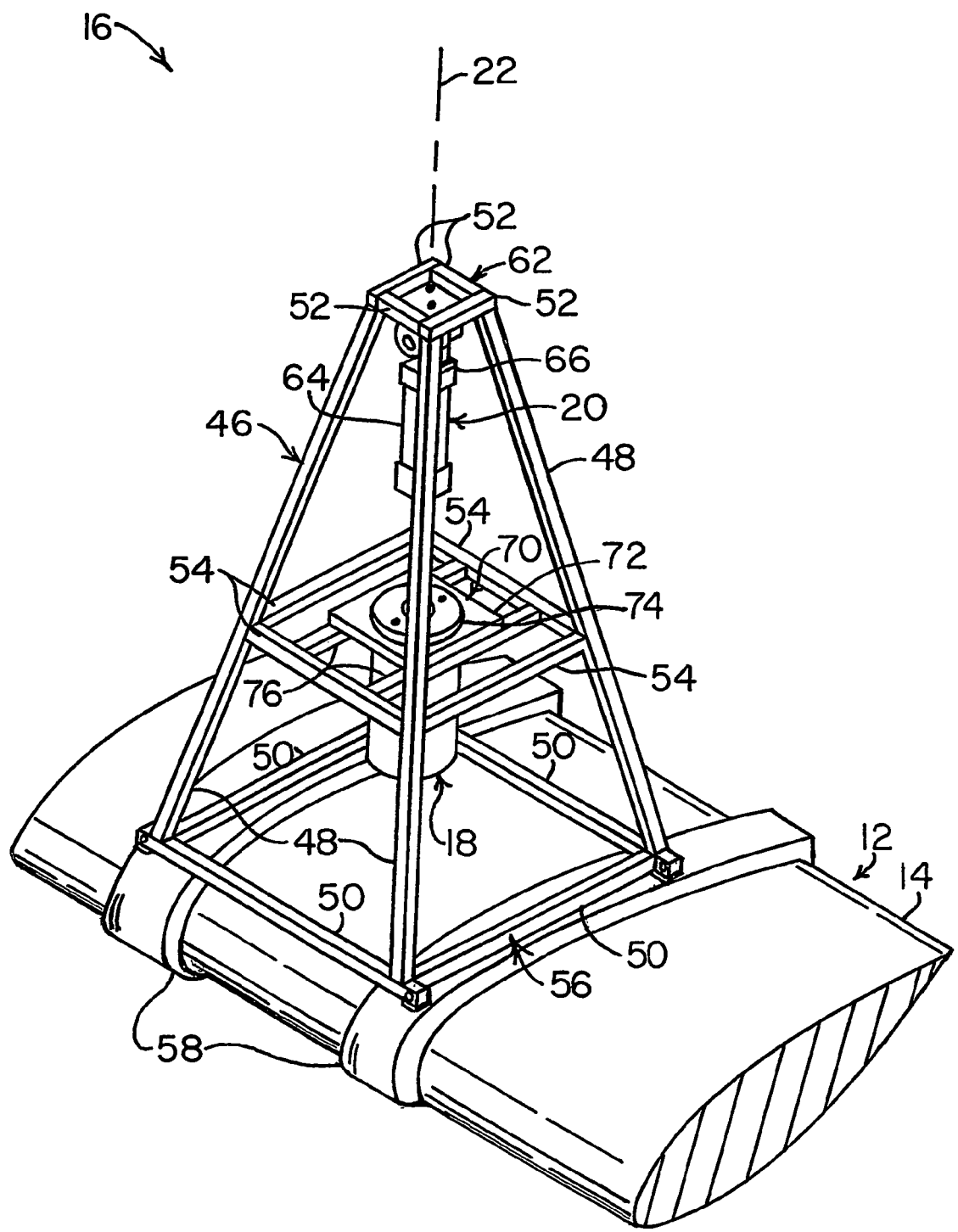
FIG. 4 is an enlarged perspective view of the load frame, mass, and mass actuator according to one embodiment of the present invention.

With reference now primarily to FIG. 4, the resonant actuator 16 may comprise a load frame 46 configured to receive the reciprocating mass 18 and the actuator 20. The load frame 46 transfers to the specimen 12 the inertial loads generated by the reciprocating mass 18. Accordingly, the load frame 46 may comprise any of a wide range of structures and configurations that are now known in the art or that may be developed in the future that would be suitable for this purpose. In one preferred embodiment, the load frame 46 comprises a pyramid-shaped structure having four support legs 48 (only three of which can be seen in FIG. 4) connected at their lower ends by cross-members 50 and at their upper ends by cross-members 52. The support legs 48 are also supported by intermediate cross-members 54 located between the lower and upper cross-members 50 and 52, respectively. The lower end 56 of the load frame 46 may be provided with any convenient means for allowing the load frame 46 to be fixedly attached to the specimen 12 (e.g., blade 14). By way of example, in one preferred embodiment, the lower end 56 of load frame 46 is affixed to a pair of blade cuffs 58 mounted to the blade 14. Alternatively, other attachment methods and devices may be used to secure the load frame 46 to the specimen 12, as would be obvious to persons having ordinary skill in the art after having become familiar with the teachings of the present invention.

The actuator 20 is mounted to the upper end 62 of the load frame 46 and is operatively associated with the mass 18 so that the mass 18 may be reciprocated along the linear displacement path 22. The actuator 20 may comprise any of a wide variety of actuators suitable for reciprocating the mass back and forth along the linear displacement path 22. In one embodiment, the actuator 20 comprises a double-acting hydraulic actuator 64, the body end 66 of which is mounted to the upper end 62 of the load frame 46 in the manner best seen in FIG. 4. The rod end 68 (not shown in FIG. 4, but shown in FIGS. 1 and 3) of hydraulic actuator 64 is connected to the mass 18. It is generally preferred, but not required, to provide a guide member 70 to the load frame 46 to assist in restraining the mass 18 so that the same does not depart appreciably from the linear displacement path 22 as it is reciprocated. By way of example, the guide member 70 in one embodiment comprises a plate 72 having a hole 74 therein sized to pass the mass 18. The plate 72 is mounted to the intermediate cross-members 54 via a pair of beams 76. Other alternative arrangements are also possible and the present invention should not be regarded as limited to the particular structural arrangement shown and described herein.

As was briefly mentioned above, it is generally preferred, but not required, to provide the apparatus 10 with a transverse load actuator system 32 for applying a transverse or "lead-lag" load to the specimen 12 (e.g., blade 14). As was the case with the resonant actuator system 16, the transverse load actuator system 32 may be mounted at any convenient position along the length of the specimen (e.g., blade 14). Accordingly, the present invention should not be regarded as limited to arrangements wherein the transverse load actuator system 32 is located at any particular position along the length of the specimen 12. However, by way of example, in one embodiment, the transverse load actuator system 32 is positioned near the resonant actuator 16 (e.g., between about $2/3$ to $3/4$ of the span of the blade 14).

With reference now primarily to FIGS. 2 and 3, the transverse load actuator system 32 may comprise an actuator 78 that is connected to the specimen 12 via a pushrod 80 and bellcrank 82. The bellcrank 82 may be pivotally mounted to a fixed trunnion 84 and transmits force and motion between the actuator 78 and the pushrod 80 in a manner well-known in the art. In the embodiment shown and described herein, the proximal and distal ends 86, 88 of pushrod 80 are provided with flexible joints 90 (e.g., universal joints) suitable for accommodating the vertical or flapping movement of the specimen 12 resulting from the action of the resonant actuator system 16. Similarly, the actuator 78 may be pivotally or flexibly mounted to the bellcrank 82 and to a fixed base plate 94, as would be obvious to persons having ordinary skill in the art after having become familiar with the teachings of the present invention.

The various components of the transverse load actuator system 32 may comprise any of a wide range of components and devices well-known in the art or that may be developed in the future that would be suitable for the intended application. Consequently, the present invention should not be regarded as limited to any particular components or devices. However, by way of example, in one embodiment, the actuator 78 may comprise a double-acting hydraulic actuator 92 the body end of which is pivotally mounted to the base plate 94 and the rod end of which is pivotally mounted to the bellcrank 82. The pushrod 80 and bellcrank 82 may be fabricated in the conventional manner from conventional materials (e.g., steel). Alternatively, of course, other fabrication methods and materials may also be used, as would be obvious to persons having ordinary skill in the art after having become familiar with the teachings of the present invention.

Depending on the objects to be achieved by the particular testing that is to be done, it may be desirable to mount one or more additional masses 44 to the specimen 12 (e.g., blade 14) in order to change the dynamic response of the specimen 12 to ensure that the loads placed thereon more accurately represent the in-service loads expected to be applied to the specimen 12. In this regard, it should be noted that the provision and placement of any such additional masses 44 will be dictated by the requirements of the test, and are not required to practice the method and apparatus of the present invention. Consequently, the present invention should not be regarded as limited to the provision of, and/or any particular placement of, such additional masses 44.

Figure 5:
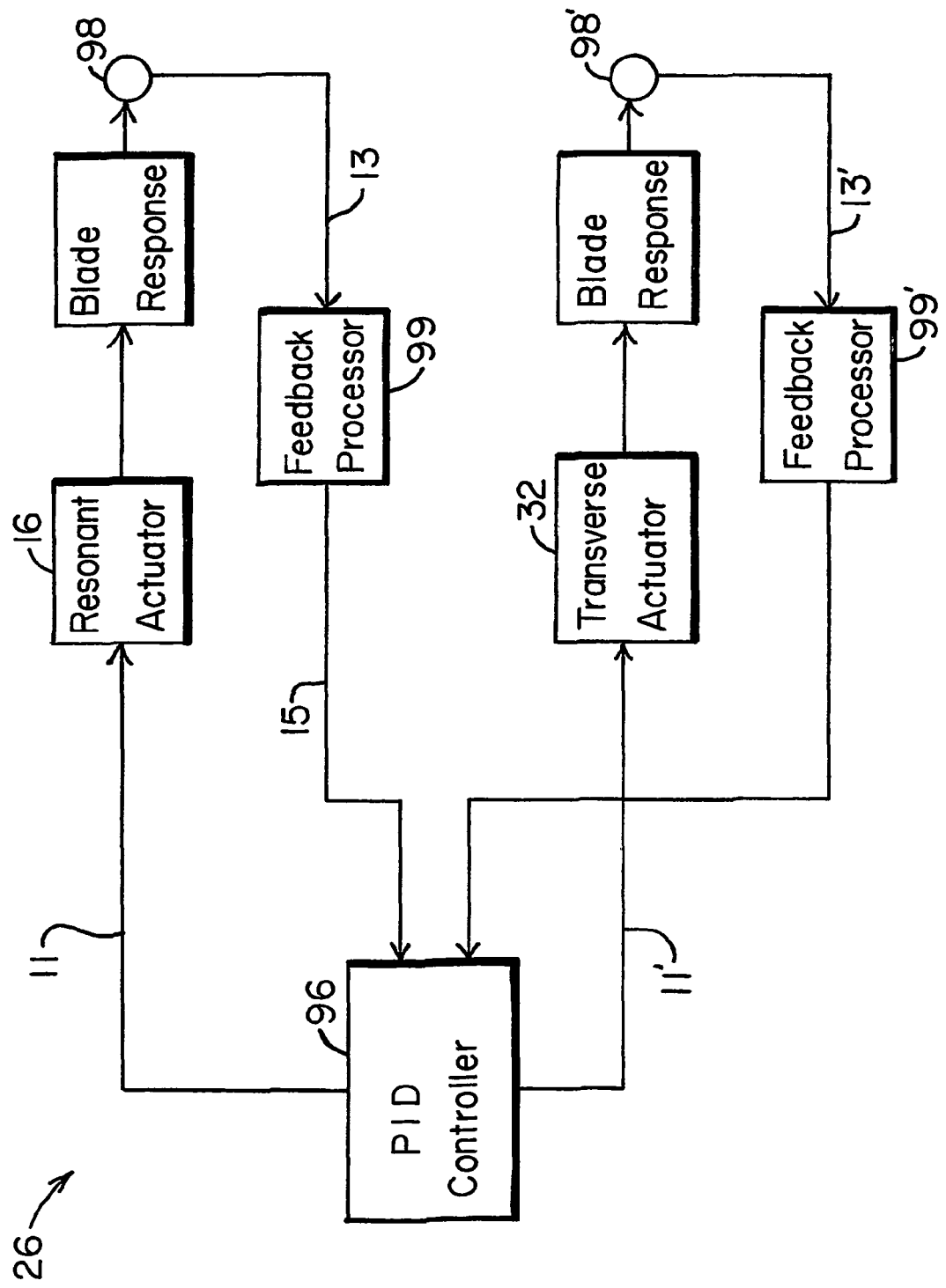
FIG. 5 is a block diagram of the control system.

Referring now to FIG. 5, the control system 26 is used to control the operation of the resonant actuator system 16 as well as the optional transverse load actuator system 32, if such a transverse load actuator system 32 is provided. In one embodiment, the control system 26 may comprise a PID (proportional integral/derivative) controller 96, a feedback sensor 98, and a feedback signal processor system 99. The PID controller 96 is operatively associated with the resonant actuator system 16 and produces an output signal 11 suitable for operating the resonant actuator system 16. For example, in the case where the resonant actuator system 16 comprises a hydraulic actuator 64 (FIG. 4), the output signal 11 from the PID controller may be used to operate hydraulic fluid flow control apparatus (e.g., a valve or valves, not shown) to cause the hydraulic actuator 64 to reciprocate the mass 18 back and forth along the displacement path 22. However, since apparatus for operating hydraulic actuators are well-known in the art and could be easily provided by persons having ordinary skill in the art after having become familiar with the teachings of the present invention, the particular apparatus that may be used as an interface between the PID controller 96 and the actuator 64 will not be described in further detail herein.

Before proceeding with the description, it should be noted that the term "resonant frequency of the specimen in a test configuration" refers to the resonance frequency of the specimen 12 (e.g., blade 14) with the various additional items associated with the present invention, or other items, connected to the specimen 12 while it is being tested. For example, in the embodiment shown and described herein, the blade 14 will have mounted to it the resonant actuator system 16, the transverse load actuator system 32, and perhaps one or more masses 44. These additional devices, systems, and masses mounted to the blade 14 will change the resonant frequency of the blade 14 from what it would be otherwise without such additional devices, systems, and masses. Consequently, in order to produce a resonant vibration or response in the blade 14, the mass 18 should be reciprocated at a reciprocation frequency that is about equal to the resonant frequency of the specimen 12 (e.g., blade 14) in the test configuration, as opposed to the "natural" resonant frequency of the specimen 12 without the additional devices, systems, and masses mounted to the specimen 12.

The resonant frequency of the specimen in the test configuration may be determined in accordance with any of a wide variety of methods now known in the art or that may be developed in the future. For example, the resonant frequency of the specimen in the test configuration may be determined by applying an impulse to the specimen 12 (e.g., blade 14), then measuring its response (i.e., vibration frequency). Alternatively, any of a wide range of analytical or numerical methods may also be used to determine the resonant frequency of the specimen (e.g., blade 14) in the test configuration. Since the resonant frequency of the specimen in the test configuration may be easily determined by persons having ordinary skill in the art after having become familiar with the teachings of the present invention, the particular method for determining the resonant frequency of the specimen or blade in the test configuration will not be described in further detail herein.

In one embodiment, the control system 26 operates the resonant actuator system 16 at a fixed frequency that is selected to be about the same as the resonant frequency of the specimen in the test configuration. That is, the reciprocation frequency of the mass 18 will be constant for a given specimen and test configuration. Generally speaking, acceptable results may be achieved by maintaining the reciprocation frequency within about 2-3 percent (1% preferred) of the resonant frequency of the specimen in the test configuration. Alternatively, the control system 26 could be operated to vary the reciprocation frequency of the mass 18 during the testing process. Therefore, the present invention should not be regarded as limited to either a constant or time-varying reciprocation frequency.

In the embodiment shown and described herein, the resonant actuator system 16 is configured to vary the displacement of the reciprocating mass 18 in order to control the bending or flap load applied to the specimen 12. While the system 16 can be operated in an "open-loop" mode (i.e., without feedback) to achieve this function, it is generally preferred to provide the system 16 with a feedback loop to allow the system 16 to be operated in a "closed-loop" mode. In one embodiment, the feedback loop may comprise a feedback sensor 98 and a feedback signal processor 99 connected in the manner illustrated in FIG. 5. The feedback sensor 98 is connected to, or is operatively associated with, the blade 14 and produces a feedback signal 13 that is directed to the feedback signal processor 99. The feedback signal processor 99 is in-turn connected the PID controller 96 and produces a processed feedback signal 15 suitable for use by the PID controller 96. The feedback system allows the control system 26 to operate the resonant actuator system 16 to achieve a desired loading of the specimen 12.

The feedback sensor 98 used to produce the feedback signal 13 may comprise any of a wide range of sensors and devices for sensing any of a wide variety of parameters from which may be obtained a useful feedback signal 13. For example, in one preferred embodiment, the feedback sensor 98 comprises an accelerometer (not shown) mounted to the blade 14 for sensing the acceleration of the blade in the bending or flap direction. Accordingly, the feedback signal 13 produced by the accelerometer will be related to the acceleration of the blade 14. The feedback signal processor system 99 will then process the feedback signal 13 as necessary to place it in a form suitable for the PID controller 96. Other arrangements are possible. For example, in another embodiment, the feedback sensor 98 may comprise one or more strain gauge sensors (also not shown) for sensing a strain in some portion of the blade 14. The feedback signal 13 produced by such strain gauge sensors will then be related to the strain produced in the blade by the deflection caused by the reciprocating mass 18. The feedback processor 99 will then process this signal as necessary to place it in a form suitable for the PID controller 96. The PID controller 96 uses the processed feedback signal 15 to control or vary the displacement of the reciprocating mass 18 (i.e., the magnitude of the movement of the mass 18 along the linear displacement path 22) in order to maintain the load on the specimen 12 at the desired level or within a desired range. Stated another way, the control system 26 allows the load placed on the specimen 12 by the resonant test system 16 to be changed or varied by varying the displacement of the reciprocating mass 18.

As mentioned above, it is generally preferred, but not required, to provide the apparatus 10 with a transverse load actuator system 32 in order to apply a load to the specimen 12 (e.g., blade 14) in a transverse direction 34. In the embodiment shown and described herein, the transverse direction 34 is orthogonal to both the longitudinal axis 24 and the linear displacement path 22. Advantageously, the transverse load actuator system 32 may be operated simultaneously with the resonant actuator system 16 in order to simultaneously apply both bending (or flap) and transverse (or lead-lag) loads to the specimen 12. Alternatively, the transverse actuator system 32 may be operated separately from the resonant actuator system 16.

Still referring to FIG. 5, the PID controller 96 may also be connected to the transverse load actuator system 32. The system may also be provided with a feedback sensor 98' and a feedback signal processor system 99'. The PID controller 96 produces an output signal 11' suitable for operating the transverse load actuator system 32 at the same frequency as the reciprocating mass 18 (which may or may not be the same as the resonance frequency of the specimen in the test configuration). Operating the transverse load actuator system 32 at the same frequency as the reciprocating mass 18 allows the same phase relationship to be maintained between the bending (or flap) and transverse (or lead-lad) loads. In the case where the transverse load actuator 78 comprises a hydraulic actuator 92 (FIG. 3), the output signal 11' from the PID controller 96 may be used to operate a hydraulic fluid flow control apparatus (e.g., a valve or valves, not shown) to cause the hydraulic actuator 92 to apply a load to the blade 14 along the transverse direction 34. More specifically, the PID controller 96 will operate the actuator 92 to apply the transverse load at the same frequency as the frequency of the reciprocating mass 18.

The magnitude of the transverse load applied by the transverse load actuator system 32 may be varied or changed by varying or changing the displacement of the transverse load actuator 78. In one embodiment, transverse load actuator system 32 may utilize the feedback sensor 98' and feedback signal processor system 99' to assist in controlling the magnitude of the transverse load applied by the transverse load actuator system 32. More specifically, the feedback sensor 98' is used to produce a feedback signal 13'. The feedback signal processor system 99' then processes the feedback signal 13' as necessary to place it in a form suitable for the PID controller 96. The feedback sensor 98' may comprise any of a wide range of sensors and devices for sensing any of a wide variety of parameters from which may be obtained a useful feedback signal 13'. For example, in one embodiment, the feedback sensor 98' comprises an accelerometer (not shown) mounted to the blade 14 for sensing the acceleration of the blade in the transverse direction 34. Accordingly, the feedback signal 13' produced by the accelerometer will be related to the acceleration of the blade 14. In another embodiment, the feedback sensor 98' may comprise one or more strain gauge sensors (also not shown) for sensing a strain in some portion or portions of the blade 14. The feedback signal produced by such strain gauge sensors will then be related to the strain produced in the blade by the transverse load actuator system 32.

It should be noted that the foregoing description of the control system 26 relates to the control system 26 that may be utilized in one embodiment of the invention. Other types of control systems having other types of components may, of course, be utilized depending on the particular embodiment of the invention that is utilized in any particular application. For example, while one embodiment of the control system 26 utilizes a PID controller 96, the use of a PID controller is not required, and other types of systems may be utilized, as would be obvious to persons having ordinary skill in the art after having become familiar with the teachings of the present invention. Still other variations are possible. For example, other embodiments of the control system 26 may utilize other types of feedback sensors and feedback loop architectures, again depending on the particular application. Accordingly, the control system 26 should not be regarded as limited to the particular types of systems, components, and arrangements shown and described herein.

The apparatus 10 may be operated as follows to place one or more structural loads on the specimen 12 under test. Assuming that a suitable specimen 12, such as a rotor or turbine blade 14, has been provided, the specimen 12 (e.g., blade 14) is mounted in a suitable test fixture 36. In one preferred embodiment, the test fixture may comprise a rigid support or mount 38 for fixedly supporting the root end 40 of the blade 14. The resonant actuator system 16 is mounted to the blade 14 at a position intermediate the root 40 and tip 42 of the blade 14 in the manner best seen in FIGS. 1 and 2. A plurality of static masses 44 are also mounted to the blade 14 in order to better approximate the expected in-service loads. The control system 26 is then activated to operate the resonant actuator system 16. More specifically, the control system 26 operates the actuator 20 to reciprocate the mass 18 at a reciprocation frequency that is about equal to the resonant frequency of the specimen 12 (e.g., blade 14) in the test configuration. The inertial loads placed on the actuator 20 by the reciprocating mass 18 are transferred to the blade 14, which results in the vibration of the blade 20 along the longitudinal axis 24. That is, the blade 14 will begin to be displaced in the directions indicated by arrows 28 and 30. Since the reciprocating frequency of the mass 18 is selected to be about equal to the resonant frequency of the blade 14 in the test configuration, the resonant actuator system 16 will easily produce substantial deflections (and resulting loads) of the blade 14 in the flap or span-wise direction. The magnitude of the bending (or flap) load applied by the resonant actuator system 16 is controlled by varying the displacement of the reciprocating mass 18. The feedback loop (comprising feedback sensor 98 and feedback processor 99) may be used to provide "closed-loop" control of the magnitude of the bending load. Alternatively, the resonant actuator system 16 system could be operated in an open-loop mode (i.e., without feedback) if so desired.

If a transverse load actuator system 32 is provided, the operator (not shown) may command the control system 26 to also actuate the transverse load actuator system 32 in order to simultaneously apply transverse loads to the vibrating blade 14. The transverse load actuator system 32 is operated at the same frequency as the reciprocating mass in order to ensure that the phase relationship is maintained between the bending (or flap) loads applied by the resonant actuator system 16 and the transverse (or lead-lag) loads applied by the transverse load actuator system 32. The magnitude of the transverse (or lead-lag) load applied by the transverse load actuator system 32 is controlled by varying the displacement of the transverse load actuator 78. The feedback loop (comprising feedback sensor 98' and feedback processor 99') may be used to provide closed-loop control of the magnitude of the transverse load. Alternatively, the transverse load actuator system 32 could be operated in an open-loop mode (i.e., without feedback) if desired.

It is contemplated that the inventive concepts herein described may be variously otherwise embodied and it is intended that the appended claims be construed to include alternative embodiments of the invention except insofar as limited by the prior art.

What is claimed is:

1. An apparatus for applying at least one cyclical load to a specimen, the specimen extending at least along a longitudinal axis, comprising:
    a mass;
    an actuator mounted to the specimen and operatively associated with said mass, said actuator moving said mass along a linear displacement path that is perpendicular to the longitudinal axis of the specimen, wherein the specimen comprises a wind turbine blade that is rigidly mounted at a root end and unsupported at a tip end and wherein the actuator is mounted at a location between the root end and the tip end of the specimen such that the moving of the mass relative to the wind turbine blade applies a bending load to the specimen; and
    a control system operatively associated with said actuator, said control system operating said actuator to reciprocate said mass along the linear displacement path at a reciprocating frequency, said reciprocating frequency being about equal to a resonance frequency of the specimen in a test configuration causing displacement of the tip relative to the longitudinal axis of the specimen.

2. The apparatus of claim 1, further comprising a feedback sensor operatively associated with said control system, said feedback sensor producing a feedback signal, said control system being responsive to the feedback signal produced by said feedback sensor, said control system operating said actuator to change a displacement of said mass in response to said feedback signal.

3. The apparatus of claim 2, wherein said feedback sensor comprises a strain gauge and wherein the feedback signal produced by said feedback sensor is related to a strain in the specimen.

4. The apparatus of claim 2, wherein said feedback sensor comprises an accelerometer and wherein the feedback signal produced by said feedback sensor is related to an acceleration of the specimen.

5. The apparatus of claim 1, further comprising a load frame mounted directly to the specimen, said actuator being mounted to said load frame.

6. The apparatus of claim 5, wherein said actuator comprises a linear hydraulic actuator having a proximal end and a distal end, the proximal end of said linear hydraulic actuator being mounted to said load frame, the distal end of said linear hydraulic actuator being mounted to said mass so that the mass moves independently of the specimen.

7. The apparatus of claim 1, further comprising a transverse load actuator operatively associated with the specimen, said transverse load actuator applying to the specimen a load in a transverse direction, said transverse direction being substantially orthogonal to the longitudinal axis of the specimen and to the linear displacement path and wherein the transverse load actuator is attached to the specimen at a location between the tip end and the root end of the specimen.

8. The apparatus of claim 7, wherein the load applied to the specimen by said transverse load actuator is varied at the reciprocating frequency.

9. The apparatus of claim 1, further comprising a static mass mounted to the specimen.

10. A system for vibrating a specimen, the specimen extending at least along a longitudinal axis from a first to a second end, comprising:
    reciprocating mass means operatively associated with the specimen for sinusoidally vibrating the specimen along the longitudinal axis at about a resonance frequency of the specimen in a test configuration, wherein the specimen is rigidly supported at the first end and unsupported at the second end and wherein the reciprocating mass means is mounted to the specimen at a location between the first and second ends; and
    displacement control means operatively associated with said reciprocating mass means for varying a vibrational displacement of the specimen,
    wherein said reciprocating mass means comprises: a mass; and actuator means operatively associated with said mass for reciprocating said mass along a displacement path that is perpendicular to the longitudinal axis of the specimen such that the mass does not contact the specimen during the reciprocating.

11. A method for vibrating a wind turbine blade specimen, the specimen extending at least along a longitudinal axis from a root to a tip, comprising:
    mounting a mass to the specimen nearer to the tip than to the root so that said mass can be reciprocated along a linear displacement path that is perpendicular to the longitudinal axis of the specimen to apply a flap load to the specimen; and
    reciprocating the mass along the linear displacement path at a reciprocation frequency that is about equal to a resonance frequency of the specimen in a test configuration, wherein the mass remains spaced apart from the specimen during reciprocating along the linear displacement path.

12. The method of claim 11, further comprising:
    detecting a strain in the specimen; and
    controlling a displacement of the mass to place a desired load on the specimen based on the detected strain.

13. The method of claim 11, further comprising:
    detecting an acceleration of the specimen; and
    controlling a displacement of the mass to place a desired load on the specimen based on the detected acceleration.

14. The method of claim 11, further comprising applying to the specimen a load in a transverse direction, the transverse direction being substantially orthogonal to the longitudinal axis of the specimen and to the linear displacement path.

15. The method of claim 14, further comprising varying the load applied to the specimen in the transverse direction at about the reciprocation frequency.

16. An apparatus for applying at least one cyclical load to a specimen, the specimen extending at least along a longitudinal axis, comprising:
    a mass;
    an actuator mounted to the specimen and operatively associated with said mass, said actuator moving said mass along a linear displacement path that is substantially perpendicular to the longitudinal axis of the specimen;

a transverse load actuator operatively associated with the specimen, said transverse load actuator applying to the specimen a cyclical load in a transverse direction, said transverse direction being substantially perpendicular to the longitudinal axis of the specimen and to the linear displacement path; and a control system operatively associated with said actuator and said transverse load actuator, said control system operating said actuator to reciprocate said mass along the linear displacement path at a reciprocating frequency, said reciprocating frequency being about equal to a resonance frequency of the specimen in a test configuration, said control system operating said transverse load actuator to vary the cyclical load at about the reciprocating frequency.

17. The apparatus of claim 16, further comprising a feedback sensor operatively associated with said control system, said feedback sensor producing a feedback signal, said control system being responsive to the feedback signal produced by said feedback sensor, said control system operating said actuator to change a displacement of said mass in response to said feedback signal.

18. The apparatus of claim 17, wherein said feedback sensor comprises at least one accelerometer.

19. The apparatus of claim 17, wherein said feedback sensor comprises at least one strain gauge.

20. The apparatus of claim 16, wherein said control system comprises a PID controller.

* * * * *